(12) United States Patent
Cooper

(10) Patent No.: US 6,924,303 B2
(45) Date of Patent: Aug. 2, 2005

(54) ANALGESIC AND ANTI-INFLAMMATORY COMPOSITIONS CONTAINING COX-2 INHIBITORS

(75) Inventor: Stephen Allen Cooper, Denville, NJ (US)

(73) Assignee: Wyeth, Madison, NY (US)

( * ) Notice: Subject to any disclaimer, the term of this patent is extended or adjusted under 35 U.S.C. 154(b) by 79 days.

(21) Appl. No.: 10/297,897

(22) PCT Filed: Jun. 13, 2001

(86) PCT No.: PCT/US01/18990

§ 371 (c)(1),
(2), (4) Date: Apr. 29, 2003

(87) PCT Pub. No.: WO01/95898

PCT Pub. Date: Dec. 20, 2001

(65) Prior Publication Data

US 2003/0216461 A1 Nov. 20, 2003

Related U.S. Application Data

(60) Provisional application No. 60/211,307, filed on Jun. 13, 2000.

(51) Int. Cl.$^7$ .................... A61K 31/415; A61K 31/19
(52) U.S. Cl. ........................ 514/406; 514/570
(58) Field of Search ................... 514/406, 570

(56) References Cited

FOREIGN PATENT DOCUMENTS

| EP | 0 868 915 A1 | 10/1998 |
|---|---|---|
| WO | WO-95/00501 A2 | 1/1995 |
| WO | WO-97/44028 A1 | 11/1997 |
| WO | WO-98/03484 A1 | 1/1998 |
| WO | WO-98/50033 A1 | 11/1998 |
| WO | WO-00/61571 A1 | 10/2000 |
| WO | WO-01/95898 A1 | 12/2001 |

OTHER PUBLICATIONS

PubMed, Clemett D, et al, Drugs 2000 Apr, 59(4):957–80, abstract.*
Frank Porreca, et al., Supraspinal and Spinal Potency of Selective Opioid Agonists in the Mouse Writhing Test, The Journal of Pharmacology and Experimental Therapeutics, p. 890–894, vol. 240, No. 3, 1987.
Database Medline on STN, No. 2000107788, Tindall, E. Celecoxib for the treatment of pain and inflammation: the preclinical and clinical results, Abstract, J. Am. Osteopathic Assoc., Nov. 1999, 99(11 Suppl), S13–7.
Database MEDLINE on STN, (Columbus, OH, USA), No. 1998379691, Schnitzer, T. J. 'Non–NSAID pharmacologic treatment options for the management of chronic pain,' abstract, Am. J. Med., Jul. 27, 1998, 105(1B), 45S–52S.
Cashman, "*The Mechanisms of Action of NSAIDs in Analgesia*" Drgus 1996; 52 Suppl. 5, pp. 13–23.
Abstract, Russian Application No. 97104487, Apr. 20, 1999, PANATsEJa Biotek Ltd.

* cited by examiner

*Primary Examiner*—Rebecca Cook
(74) *Attorney, Agent, or Firm*—Darby & Darby

(57) ABSTRACT

The present invention is directed to an analgesic composition which consists essentially of a cyclooxygenase-2 inhibitor and a compound selected from the group consisting of non-steroidal anti-inflammatory drugs, acetaminophen and mixtures thereof. The present invention further is directed to a method for inducing analgesia through the administration of such a composition to a patient.

9 Claims, No Drawings

ANALGESIC AND ANTI-INFLAMMATORY COMPOSITIONS CONTAINING COX-2 INHIBITORS

This application claims the benefit of U.S. Provisional Application No. 60/211,307, filed Jun. 13, 2000, and is the National Stage of International Application No. PCT/US01/18990 filed Jun. 13, 2001.

FIELD OF THE INVENTION

This invention relates to a composition for alleviating pain and/or inflammation which provides both quick onset and long duration. More particularly, this invention is concerned with a composition consisting essentially of a cyclooxygenase-2 inhibitor (also referred to as a cyclooxygenase II, COX-2 or COX II inhibitor) and a second analgesic composition selected from the group consisting of NSAIDS (non-steroidal, anti-inflammatory drugs), acetaminophen and mixtures thereof. The invention is also directed to a method for alleviating pain and/or inflammation through the administration of such composition.

BACKGROUND OF THE INVENTION

Compounds have been found which exhibit anti-inflammatory, analgesic and antipyretic activity, (in addition to inhibiting hormone-induced uterine contractions and certain types of cancer growth) through inhibition of prostaglandin G/H synthase, also known as cyclooxygenase. Initially, only one form of cyclooxygenase was known, this corresponding to cyclooxygenase-1 or the constitutive enzyme, as originally identified in bovine seminal vesicles. This enzyme has been cloned, sequenced and characterized from various sources including sheep, mouse and man. Prostaglandins have also been found to have both physiological and pathological roles. Cyclooxygenase-1 is responsible for endogenous basal release of prostaglandins and is important in their physiological functions such as the maintenance of gastrointestinal integrity and renal blood flow. Non-steroidal anti-inflammatory drugs (NSAIDS) have been found to inhibit the cyclooxygenase-1 enzyme and thereby exhibit anti-inflammatory, analgesic and anti-pyretic properties.

While NSAIDS exhibit excellent anti-inflammatory, analgesic and antipyretic properties and possess additional benefits such as quick onset times, NSAIDS have a potential for gastrointestinal toxicity, and/or renal side effects.

More recently, the gene for a second inducible form of cyclooxygenase, referred to as cyclooxygenase-2, has been cloned, sequenced and characterized in chicken, marine and human sources. This gene, termed cyclooxygenase-2, is rapidly and readily inducible by a number of agents including mitogens, endotoxin, hormones, cytokines and growth factors. In contrast to cyclooxygenase-1, cyclooxygenase-2 is mainly responsible for the pathological effects of prostaglandins where rapid induction of the enzyme would normally occur in response to such agents as inflammatory agents, hormones, growth factors, and cytokines. Therefore, a selective inhibitor of cyclooxygenase-2 has similar anti-inflammatory, analgesic and antipyretic properties to those obtained by inhibition of the cyclooxygenase-1 through use of an NSAIDS.

A number of cyclooxygenase-2 inhibitors are known. For example, cyclooxygenase-2 inhibitors are disclosed in U.S. Pat. Nos. 5,393,790; 5,409,944; 5,418,254; 5,420,343; 5,436,265; 5,474,995; 5,476,944; 5,486,534; 5,510,368; 5,521,213; 5,536,752; 5,547,975; 5,550,142; 5,552,422; 5,565,482; 5,576,339; 5,580,985; 5,585,504; 5,593,994 and 5,596,008.

While cyclooxygenase-2 inhibitors possess similar anti-inflammatory, analgesic and antipyretic activity to NSAIDS, cyclooxygenase-2 inhibitors also exhibit a diminished tendency to induce some of the mechanism-based side effects that may occur with the use of NSAIDs. In particular, cyclooxygenase-2 inhibitors appear to have a reduced potential for gastrointestinal toxicity and renal side effects, a reduced effect on bleeding times and possibly a diminished ability to induce asthma attacks in aspirin-sensitive asthmatic subjects.

However, while cyclooxygenase-2 inhibitors do possess potential benefits relating to reduced side effects, they are generally slow acting relative to cyclooxygenase-1 inhibitors such as NSAIDs or acetaminophen. Therefore, a patient using them for analgesia perceives that they possess an unsatisfactorily long onset period in providing the desired analgesia.

The compositions claimed herein offer the benefits of quicker onset for analgesia relative to cyclooxygenase-2 inhibitors used alone. The claimed compositions further reduce the amount of cyclooxygenase-1 inhibitors administered and thereby reduce the potential for gastrointestinal toxicity. Such combinations further provide longer duration of action, such as "once daily dosing", without losing the benefit of the fast onset of analgesia associated with the use of cyclooxygenase-1 inhibitors. In still a further benefit of the present invention, the combinations of the claimed compositions are found to be synergistic in that the onset time of the cyclooxygenase-1 inhibitors (and therefore the claimed composition) is reduced relative to the onset times of either component used alone. In other words, the onset of the cyclooxygenase-1 inhibitor component (e.g. NSAID) is unexpectedly potentiated by the presence of the cyclooxygenase-2 inhibitor.

SUMMARY OF THE INVENTION

In accordance with the present invention, a composition for alleviating pain and/or inflammation is provided which consists essentially of (a) at least one cyclooxygenase-2 inhibitor and (b) at least one compound selected from the group consisting of NSAIDs, acetaminophen and mixtures thereof.

Further in accordance with this invention, a method of alleviating pain and/or inflammation is provided which comprises administering to a mammal exhibiting pain a composition consisting essentially of (a) at least one cyclooxygenase-2 inhibitor and (b) at least one compound selected from the group consisting of NSAIDs, acetaminophen and mixtures thereof.

DESCRIPTION OF THE PREFERRED EMBODIMENTS

The method of the claimed invention and the therapeutic composition therefore are applicable to the treatment of all varieties of pain. The term "pain-alleviating" shall be understood herein to include the expressions "pain-suppressing" and "pain-inhibiting" as the invention is applicable to the alleviation of existing pain as well as the suppression or inhibition of pain which would otherwise ensue from an imminent pain-causing event. Any of the cyclooxygenase-2 inhibitors heretofore used to alleviate pain can be used herein.

The expression "analgesia-inducing amount" as applied to the cyclooxygenase-1 inhibitors and/or cyclooxygenase-2 inhibitors employed in the therapeutic method and composition of this invention shall be understood to mean an amount thereof which when administered provides significant analgesic activity.

Specific cyclooxygenase-2 inhibitors that can be used in the practice of this invention are those compounds having a duration of activity of at least 12 hours. These include celecoxib, rofecoxib, meloxicam and nimesulide. Especially preferred are celecoxib and rofecoxib.

Celecoxib is 4-[5-(4-methylphenyl)-3-(trifluoromethyl)-1H-pyrazol-1-yl]benzenesulfonamide and is currently manufactured by G.D. Searle & Co. It is marketed under the tradename Celebrex.® Rofecoxib is 4-[4-(methylsulfonyl)phenyl]-3-phenyl-2(5H)-furanone and is currently manufactured by Merck & Co., Inc. It is marketed under the tradename Vioxx®. Meloxicam is 4-hydroxy-2-methyl-N-(5-methyl-2-thiazolyl)-2-H-1,2-benzothiazine-3-carboxamide 1,1-dioxide. Its manufacture is disclosed in U.S. Pat. No. 4,233,299, the contents of which are hereby incorporated by reference. It is approved for marketing in the United States under the tradename Mobic®. Nimesulide is N-(44-nitro-2-phenoxyphenyl)methanesulfonamide. Its manufacture is disclosed in U.S. Pat. No. 3,840,597, the contents of which are hereby incorporated by reference.

With regard to the cyclooxgenase-1 inhibitor component, any of the NSAIDS, acetaminophen, or mixtures thereof used to alleviate pain may be used. The NSAIDS for use in the compositions and methods of the present invention can be selected from the following categories:
(1) the propionic acid derivatives;
(2) the acetic acid derivatives;
(3) the fenamic acid derivatives;
(4) the biphenylcarboxylic acid derivatives; and
(5) the oxicams.

The propionic acid derivatives for use herein include, but are not limited to, ibuprofen, naproxen, flurbiprofen, fenoprofen, fenbufen, ketoprofen, pirprofen, carprofen, oxaprozin, pranoprofen, miroprofen, tioxaprofen, suprofen, alminoprofen, tiaprofenic acid, fluprofen and bucloxic acid. The propionic acid derivatives as herein defined are derivatives having a free —CH(CH$_3$)COOH or —CH$_2$CH$_2$COOH group (which optionally can be in the form of a pharmaceutically acceptable salt group, e.g. —CH(CH$_3$)COO$^-$Na$^+$ or —CH$_2$CH$_2$COO$^-$Na$^+$), typically attached directly or via a carbonyl function to a ring system, preferably to an aromatic ring system. Structurally related propionic acid derivatives having similar analgesic and anti-inflammatory properties are also intended to be encompassed by this group. Presently preferred members of the propionic acid group include ibuprofen, naproxen, flurbiprofen, fenoprofen, ketoprofen and fenbufen. Included within the description of propionic acid derivatives are isolated isomeric forms such as S+ ibuprofen as disclosed in U.S. Pat. No. 4,851,444, the contents of which are hereby incorporated by reference. Also within the practice of the present invention are the pharmaceutically acceptable salts thereof, e.g. naproxen sodium.

The acetic acid derivatives for use herein include, but are not limited to, indomethacin, tolmetin, diclofenac, fenclofenac, alclofenac, ibufenac, isoxepac, furofenac, tiopinac, zidometacin, acetmitacin, fentiazac, clidanac and oxpinac. The acetic acid derivatives as herein defined are derivatives having a free —CH$_2$COOH group (which optionally can be in the form of a pharmaceutically acceptable salt group, e.g. —CH$_2$COO$^-$Na$^+$), typically attached directly to a ring system, preferably to an aromatic or heteoaromatic ring system. Structurally related acetic acid derivatives having similar analgesic and anti-inflammatory properties are also intended to be encompassed by this group.

The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. The fenamic acid derivatives as defined herein may contain a pendant —COOH group or a pharmaceutically acceptable salt thereof e.g. in the form of a —COO$^-$N$^+$ group.

The biphenylcarboxylic acid derivatives for use herein include, but are not limited to, flufenisal and diflunisal. Structurally related biphenylcarboxylic acid derivatives having similar analgesic and/or anti-inflammatory properties are also intended to be encompassed by this group. The fenamic acid derivatives as defined herein contain a pendant —COOH group or a pharmaceutically acceptable salt thereof e.g. in the form of a —COO$^-$Na$^+$ group.

The oxicams for use herein include, but are not limited to, piroxicam, sudoxicam, tenoxicam and isoxicam. Structurally related oxicams derivatives having similar analgesic and/or anti-inflammatory properties are also intended to be encompassed by this group.

Acetaminophen is 4'-hyroxyacetanilide. It is widely marketed, including by McNeil under the tradename Tylenol®.

Especially preferred are ibuprofen, S+ ibuprofen, ketoprofen, naproxen and acetaminophen.

With regard to dosage levels, the cyclooxygenase-2 inhibitor must be present in an analgesia-inducing amount and/or pain-alleviating amount. Of the preferred mounts ranging from about 25 to about 200 mg. Preferably it is present in amounts ranging from about 100 to about 200 mg. Rofecoxib maybe present in the claimed compositions in amounts ranging from about 12.5 to about 50 mg. Preferably it is present in amounts ranging from about 25 to about 50 mg. Nimesulide may be present in the claimed compositions in amounts ranging from about 50 to about 300 mg. Preferably it is present in amounts ranging from about 100 about 200 mg. Most preferably, it is present in an amount of about 200 mg. Meloxicam may be present in the claimed compositions in amounts ranging from about 3 to about 15 mg. Preferably, it is present in amounts ranging from about 10 to about 15 mg. Most preferably, it is present in an amount of about 15 mg.

With regard to dosage levels of the cyclooxygenase-1 component of the claimed composition, it too must be present in an analgesia-inducing or pain-alleviating amount. Of the cyclooxygenase-1 inhibitors useful in the practice of the present invention, including those that are mentioned as being preferred, ibuprofen may be present in the claimed compositions in amounts ranging from about 50 to about 400 mg. Preferably it is present in amounts ranging from about 200 to about 400 mg. Most preferably, it is present in an amount of about 400 mg. Ketoprofen may be present in the claimed compositions in amounts ranging from about 6.5 to about 25 mg. Preferably it is present in amounts ranging from about 12.5 to about 25 mg. Most preferably, it is present in an amount of about 25 mg. Flurbiprofen may be present in the claimed compositions in amounts ranging from about 12.5 to about 50 mg. Preferably it is present in amounts ranging from about 25 to about 50 mg. Most preferably, it is present in an amount of about 50 mg. Fenoprofen may be present in the claimed compositions in amounts ranging from about 50 to about 100 mg. Preferably it is present in amounts ranging from about 100 to about 200 mg. Most preferably, it is present in an amount of about 200 mg. Etodolac may be present in the claimed compositions in amounts ranging from about 100 to about 400 mg. Preferably it is present in amounts ranging from about 200 to about 400 mg. Most preferably, it is present in an amount of about 400 mg. Naproxen sodium may be present in the claimed compositions in amounts ranging from about 110 to about 440 mg. Preferably it is present in amounts ranging from about 200 to about 440 mg. Most preferably, it is present in an amount of about 220 mg. Oxaprozin may be present in the claimed compositions in amounts ranging from about 100 to about 1200 mg. Preferably it is present in amounts ranging from about 300 to about 900 mg. Most preferably, it is present in an amount of about 600 mg. Piroxicam may be present in the claimed compositions in amounts ranging from about 2.5 to about 40 mg. Preferably it is present in amounts ranging from about 10 to about 40 mg. Most preferably, it is present in an amount of about 20 mg. Diclofenac may be present in the claimed compositions in amounts ranging from about 12.5 to about 75 mg. Preferably it is present in amounts ranging from about 25 to about 75 mg. Most preferably, it is present in an amount of about 50 mg.

If acetaminophen is to be used in the composition as a cyclooxygenase-1 inhibitor, it may be present in the claimed compositions in amounts ranging from about 200 to about 1000 mg. Preferably it is present in amounts ranging from about 500 to about 1000 mg. Most preferably, it is present in an amount of about 1000 mg.

While the cyclooxygenase-2 inhibitor and the cyclooxygenase-1 inhibitor need not be administered in a single tablet or other dosage unit, they must both be present in the patient at effective levels at the same time. While it is within the scope of the invention to administer the components of the claimed composition separately, as a matter of convenience, it is preferred that they be co-administered as a single therapeutic composition. All modes of administrations are contemplated, e.g., orally, rectally, intranasally, sublingual, topically, or by intravenous, intramuscular, intrasternal or subcutaneous injection. The formulations may, where appropriate, be conveniently presented in discrete dosage units and may be prepared by any of the methods well known in the art of pharmacy.

The claimed composition will ordinarily be formulated with one or more pharmaceutically acceptable ingredients in accordance with known and established practice. Thus, the composition can be formulated as a liquid, powder, suspension or elixir. Formulations for oral use can be provided as tablets, liquigel (Tm of R. P. Scherer) or hard capsules herein the pharmacologically active ingredients are mixed with an inert solid diluent such as calcium carbonate, calcium phosphate or kaolin, or as soft gelatin capsules wherein the active ingredients are mixed with water or miscible solvents such as propylene glycol; PEG's and ethanol, or an oleaginous medium, e.g., peanut oil, liquid paraffin or olive oil.

For topical administration in the mouth, the pharmaceutical compositions may take the form of buccal or sublingual tablet, drops or formulated in conventional manner.

For topical administration to the epidermis the compounds of the invention may be formulated as creams, gels, ointments, sprays or lotions or as transdermal patches. Such compositions may, for example, be formulated with an aqueous or oily base with the addition of suitable thickening, gelling, emulsifying, stabilizing, dispersing, suspending, and/or coloring agents.

The compounds of the invention may be formulated for parenteral administration by injection, conveniently intravenous, intramuscular or subcutaneous injection, for example by bolus injection or continuous intravenous infusion. Formulations for injection may be presented in unit dosage from e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas. e.g. containing conventional suppository bases such as cocoa butter or other glyceride.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethyleneoxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

The following Examples demonstrate various embodiments of the claimed invention. However, they should not be construed as limiting its scope.

EXAMPLES

Example 1

A modification of the acetic acid-induced writhing test (as disclosed in Porreca, F., H. I. Mosberg, J. R. Omnaas, T. F. Burks and A. Cowan in Supraspinal and spinal potency of selective opioid agonists in the mouse writhing test (*Journal of Pharmacology and Experimental Therapeutics* 240: 890–894, 1987)) was conducted. The mouse writhing model as described is commonly used to investigate analgesic efficacy and potential synergism with combinations of drugs.

Male Swiss mice weighing 25–30 g were obtained from Ace Laboratories. They were each placed in individual rectangular observation boxes and allowed to acclimate for at least 1 hour. A placebo vehicle of 1% Tween 80/water was prepared.

Groups of 8–10 mice each received the test agent or placebo vehicle (in an amount of 0.25 ml/25 grams of body weight) orally via stomach tube. Those mice that received the placebo vehicle composed the control group. After 20, 30, 40 or 60 minutes, each mouse was injected parenterally with a 0.6% acetic acid solution (0.25 ml/25 g body weight).

After a further 5 minutes, the number of abdominal writhes displayed by each animal was counted over a ten minute period. The number of writhes displayed by each animal in such 10 minute test period was then normalized to the mean number shown by the control (vehicle) group. Percent inhibition of writhing was expressed as:

$$\frac{(\text{Mean writhes in control group}) - (\text{Writhes by individual mouse}) \times 100}{(\text{Mean writhes in control group})}$$

Results

A preliminary study was conducted at +30 minutes to establish antinociceptive dose-response curves for ibuprofen (obtained from Sigma Chemical) and celecoxib (manufactured by G.D. Searle & Co. in 200 mg capsules and marketed under the trademark Celebrex®), respectively. The results are presented in Table 1 below. An oral $A_{50}$ value of 29.07 mg/kg (17.57–40.58) (95% confidence limits) was obtained for ibuprofen. The corresponding value for celecoxib was >80 mg/kg.

TABLE 1

| Compound | Dose (mg/kg) | Mean % inhibition ± s.e.m. |
| --- | --- | --- |
| Ibuprofen | 20 | 38.7 ± 11.2 |
|  | 40 | 59.4 ± 9.58 |
|  | 80 | 74.0 ± 4.68 |
| Celecoxib | 20 | 7.5 ± 3.38 |
|  | 40 | 21.7 ± 4.17 |
|  | 80 | 28.3 ± 8.34 |

To study the effects of the administration of the compounds in combination, one group of mice (n=8–10) received 29 mg/kg of ibuprofen followed immediately by an essentially inactive dose of celecoxib (20 mg/kg). A second group of mice (n=8–10) received 29 mg of ibuprofen followed immediately by the placebo vehicle. At either +20, +40 or +60 minutes following administration, the animals were injected i.p. with 0.6% acetic acid (0.25 ml/25 g body weight) and run in the writhing test. The data obtained are shown in Table 2.

TABLE 2

| Compound | Time (min) | Mean % inhibition ± s.e.m. |
| --- | --- | --- |
| Ibuprofen + vehicle | 20 | 36.4 ± 3.2 |
| Ibuprofen + celecoxib | 20 | 63.2 ± 8.7 |
| Ibuprofen + vehicle | 40 | 14.1 ± 6.2 |
| Ibuprofen + celecoxib | 40 | 52.7 ± 9.6 |
| Ibuprofen + vehicle | 60 | 27.3 ± 8.2 |
| Ibuprofen + celecoxib | 60 | 63.6 ± 9.2 |

It is clear from the data in Tables 1 and 2 that the presence of even an essentially inactive dose of celecoxib potentiated the ibuprofen through faster onset and duration of action.

Example 2

Tablets having the following formulations were manufactured in accordance with general tablet manufacturing processing.

| Ingredient | mg/tablet | % w/w |
| --- | --- | --- |
| Formula I | | |
| Ibuprofen | 200 | 38.6 |
| Celecoxib | 100 | 19.3 |
| Pregelantinized Starch | 75 | 14.5 |
| Microcrystalline Cellulose | 60 | 11.6 |
| Lactose, hydrous | 50 | 9.7 |
| Croscarmellose Sodium | 20 | 3.9 |
| Colloidal Silicone Dioxide | 5 | 1.0 |
| Sodium Lauryl Sulfate | 3 | 0.6 |
| Stearic Acid | 5 | 1.0 |
| Formula II | | |
| Ketoprofen | 12.5 | 4.8 |
| Celecoxib | 100 | 38.5 |
| Pregelantinized Starch | 40 | 15.4 |
| Microcrystalline Cellulose | 50 | 19.3 |
| Lactose, hydrous | 40 | 15.4 |
| Croscarmellose Sodium | 10 | 3.9 |
| Colloidal Silicone Dioxide | 2.5 | 1.0 |
| Sodium Lauryl Sulfate | 2 | 0.8 |
| Stearic Acid | 2.6 | 1.0 |
| Formula III | | |
| Ibuprofen | 200 | 52.2 |
| Refocoxib | 25 | 3.3 |
| Pregelantinized Starch | 60 | 15.6 |
| Microcrystalline Cellulose | 60 | 15.6 |
| Lactose, hydrous | 25 | 6.5 |
| Croscarmellose Sodium | 15 | 3.9 |
| Colloidal Silicone Dioxide | 4 | 1.0 |
| Sodium Lauryl Sulfate | 3 | 0.8 |
| Stearic Acid | 4 | 1.0 |
| Formula IV | | |
| Ketoprofen | 12.5 | 6.0 |
| Refocoxib | 25 | 6.0 |
| Pregelantinized Starch | 30 | 14.4 |
| Microcrystalline Cellulose | 100 | 48 |
| Lactose, hydrous | 40 | 19.2 |
| Croscarmellose Sodium | 8 | 3.2 |
| Colloidal Silicone Dioxide | 2 | 1.0 |
| Sodium Lauryl Sulfate | 1.5 | 0.7 |
| Stearic Acid | 2 | 1.0 |

What is claimed is:

1. A composition consisting essentially of (a) celecoxib and (b) ibuprofen.

2. The composition of claim 1 wherein celecoxib is present in amounts ranging from about 25 to about 200 mg and ibuprofen is present in amounts ranging from about 50 to about 800 mg.

3. The composition of claim 1 wherein celecoxib is present in amounts ranging from about 100 to about 200 mg and ibuprofen is present in amounts ranging from about 200 to about 400 mg.

4. The composition of claim 1 wherein celecoxib is present in an amount of about 200 mg and ibuprofen is present in an amount of about 400 mg.

5. A method of alleviating pain and/or inflammation comprising administering to a mammal exhibiting pain, an analgesia-inducing amount of a composition consisting essentially of (a) celecoxib and (b) ibuprofen.

6. The method of claim 5 wherein celecoxib is present in amounts ranging from about 25 to about 200 mg and ibuprofen is present in amounts ranging from about 50 to about 800 mg.

7. The method of claim 5 wherein celecoxib is present in amounts ranging from about 100 to about 200 mg and ibuprofen is present in amounts ranging from about 200 to about 400 mg.

8. The method of claim 5 wherein celecoxib is present in an amount of about 200 mg and ibuprofen is present in an amount of about 400 mg.

9. A method of potentiating ibuprofen thereof by administering celecoxib concurrently therewith to a mammal exhibiting pain, wherein the ibuprofen and the celecoxib are each administered in an analgesia-inducing amount.

* * * * *

UNITED STATES PATENT AND TRADEMARK OFFICE
CERTIFICATE OF CORRECTION

PATENT NO. : 6,924,303 B2
APPLICATION NO. : 10/297897
DATED : August 2, 2005
INVENTOR(S) : Stephan Allen Cooper It is certified that error appears in the above-identified patent and that said Letters Patent is hereby corrected as shown below:

On the title page, Item (73)
Assignee name:

Please delete "Madison, New York" and substitute

-- Madison, New Jersey --.

Signed and Sealed this

Eleventh Day of July, 2006

JON W. DUDAS
*Director of the United States Patent and Trademark Office*